United States Patent
Dekker et al.

(10) Patent No.: US 10,209,243 B2
(45) Date of Patent: Feb. 19, 2019

(54) CARDIOMYOCYTE CONTAINING DEVICE, MANUFACTURING METHOD AND MEASURING METHOD

(75) Inventors: Ronald Dekker, Eindhoven (NL); Anja Van De Stolpe, Eindhoven (NL); Berent Jan Van Meer, Eindhoven (NL); Saeed Khoshefetrat Pakazad, Eindhoven (NL); Angel Savov, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 575 days.

(21) Appl. No.: 13/813,970

(22) PCT Filed: Jul. 13, 2011

(86) PCT No.: PCT/IB2011/053130
§ 371 (c)(1),
(2), (4) Date: Feb. 4, 2013

(87) PCT Pub. No.: WO2012/017343
PCT Pub. Date: Feb. 9, 2012

(65) Prior Publication Data
US 2013/0137132 A1    May 30, 2013

(30) Foreign Application Priority Data
Aug. 5, 2010  (EP) .................................... 10172056

(51) Int. Cl.
*B01L 1/00*   (2006.01)
*B01L 3/00*   (2006.01)
(Continued)

(52) U.S. Cl.
CPC ......... *G01N 33/5061* (2013.01); *D06F 75/22* (2013.01)

(58) Field of Classification Search
CPC ...... C12M 35/04; C12M 23/26; C12M 25/02; C12M 25/06
See application file for complete search history.

(56) References Cited

U.S. PATENT DOCUMENTS 6,730,199 B1 * 5/2004 Hanni et al. ............ 204/403.02
7,611,852 B2   11/2009 Thomson et al.
(Continued)

FOREIGN PATENT DOCUMENTS

| EP | 2218722 | 8/2010 |
|----|---------|--------|
| WO | WO2003014291 | 2/2003 |
| WO | WO2005108547 | 11/2005 |

OTHER PUBLICATIONS

A.A. Werdich et al., "A Microfluidic Device to Confine a Single Cardiac Myocyte in a Sub-Nanoliter Volume or Planar Microelectrodes for Extracellular Potential Recordings", Lab on a Chip, Royal Society of Chemistry, Jan. 1, 2004, vol. 4, No. 4, pp. 357-362.

(Continued)

*Primary Examiner* — Nathan A Bowers

(57) ABSTRACT

Disclosed is a device (100) for cardiac electrophysiology screening comprising a substrate (10) comprising a cavity (42), said substrate carrying a deformable layer (32) extending over said cavity (42), wherein a portion of said deformable layer (32) covers said cavity and acts as a membrane over said cavity (32), said portion having a surface comprising a pattern of grooves (44) and carrying a multi-electrode structure (110, 110'); and a plurality of cardiomyocytes (130) assembled in at least some of said grooves (44). A method of manufacturing such a device (100) is also disclosed.

9 Claims, 18 Drawing Sheets

(51) Int. Cl.
*G01N 33/50* (2006.01)
*D06F 75/22* (2006.01)

(56) References Cited

U.S. PATENT DOCUMENTS

| | | | |
|---|---|---|---|
| 8,506,793 B2* | 8/2013 | Dekker et al. | 205/792 |
| 2007/0059763 A1* | 3/2007 | Okano et al. | 435/7.1 |
| 2007/0066911 A1 | 3/2007 | Klingenbeck-Rega | |
| 2009/0205201 A1* | 8/2009 | Xu et al. | 29/825 |
| 2011/0250585 A1* | 10/2011 | Ingber et al. | 435/5 |

OTHER PUBLICATIONS

Z. Feng et al., "An Electro-Tensile Bioreactor for 3-D Culturing of Cardiomyocytes", IEEE Engineering in Medicine and Biology Magazine, Jul. 1, 2005, pp. 73-79.

* cited by examiner

CARDIOMYOCYTE CONTAINING DEVICE, MANUFACTURING METHOD AND MEASURING METHOD

FIELD OF THE INVENTION

The present invention relates to a device for in vitro cardiac electrophysiology screening.

The present invention further relates to a method of manufacturing such a device.

The present invention yet further relates to a method of determining the cardiotoxicity of a chemical compound using such a device.

BACKGROUND OF THE INVENTION

Many drugs have cardiotoxic side effects, e.g. arrhythmias or negative effects on the contractive capacity of the heart muscle. Over the last years it has become evident that a common side-effect of a number of drugs is a prolonging effect on the QT interval in the cardiac cycle, which is an important cause of drug-induced life threatening arrhythmias. For instance, during the past years, the development of several drugs has been aborted in late phases of preclinical testing or clinical trials, and even post-marketing due to undesirable effects on the QT interval of the surface electrocardiogram (ECG). A prolongation of this interval to more than 440 to 460 msec may allow life threatening arrhythmias, e.g. torsade de pointes (TdP), to occur and has been associated with a wide variety of drugs.

This was acknowledged in 1998 when the Food and Drug Administration (FDA) defined prolongation of the QT interval as a major drug safety issue. Subsequently, identification of QT prolongation and clinical torsade de pointes has led to the removal of several drugs from the market in the United States, including terfenadine, astemizole, thioridazine, and grepafloxacin, while many others have been required by the FDA to carry additional safety labeling warning of the potential risk. Currently, assessing risk for delayed ventricular repolarization and QT interval prolongation is part of the standard pre-clinical evaluation of NCE's as adopted by the FDA and EMEA for all drugs in development.

Unfortunately, currently available preclinical in-vitro cell-based model systems for drug development and cardiotoxicity evaluation are inadequate for detecting the majority of these side-effects, while predictive in-vivo animal studies are very expensive, as well as ethically challenged. In addition, cardiotoxicity results obtained from animal studies cannot be easily extrapolated to humans.

The testing process is further complicated by the fact that these cardiotoxic effects of drugs may only become apparent during actual cardiac muscle stretching and contraction as occurs in vivo in the beating heart, especially during (strenuous) physical exercise; and in cardiac diseases associated with cardiac overload, e.g. heart failure. Currently no adequate in vitro testing model systems exist that simulate a normal beating heart, in either a physiological situation, i.e. a stretch-contraction cycle, or a pathophysiological situation, such as excessive stretch against increased pressure, associated with cardiac failure. Moreover, different drugs can have different negative effects on the heart function.

Such a testing model system should preferably be a human model system. Some human cell-based model systems are available for cardiotoxicity testing. These model systems typically consist of human embryonic stem cell (HESC)-derived cardiomyocytes, on standard multi-electrode arrays. However the usefulness of these systems is constrained by the fact that these are static model systems not taking into account the dynamics of the beating heart and the heart during exercise.

In 'An Electro-Tensile Bioreactor for 3-D Culturing of Cardiomyocytes' by Zhonggang Feng et al. in IEEE Engineering in Medicine and Biology Magazine, July/August 2005, pages 73-79, a bioreactor is disclosed which allows for the in-plane stretching of a cardiomyocyte-containing gel layer disposed on a stretchable silicone plate to simulate the mechanical and electrical response of the myocardium in vivo. A drawback of this device is that it is quite complex and not particularly suitable for in vitro cardiac electrophysiology screening due to the fact that the cardiomyocytes are embedded in a gel. Moreover the electrical activity of the cardiomyocytes cannot be measured, which is crucial to identify the action potential prolongation. Hence, there exists a need for a, preferably human, cardiomyocyte-containing device that can be used for in vitro cardiac electrophysiology screening and that can manufactured in a reproducible manner.

Similarly no adequate in vitro dynamic heart model systems exist for typically human heart diseases with a genetic component, like for example familial cardiac hypertrophy and certain cardiac arrhythmias.

SUMMARY OF THE INVENTION

The present invention seeks to provide an improved device for in vitro cardiac electrophysiology screening.

The present invention further seeks to provide a method of manufacturing such an improved device.

The present invention yet further seeks to provide a method of determining the electrophysiological response of cardiomyocytes to a chemical compound using such an improved device.

According to a first aspect of the present invention, there is provided a device for determining in vitro cardiac electrophysiology g, comprising a substrate comprising a cavity, said substrate carrying a deformable layer extending over said cavity, wherein a portion of said deformable layer covers said cavity, said portion having a surface comprising a pattern of grooves and carrying an electrode structure and an adhesive coating; and a plurality of cardiomyocytes adhered to said coating and assembled in at least some of said grooves.

The presence of the cavity ensures that at least the central region of the deformable layer, e.g. an elastomer layer, is not attached to the substrate, such that this region can move freely, e.g. as triggered by a contraction of the cardiomyocytes. In addition, this arrangement facilitates an out-of-plane deformation of the deformable layer, contrary to the in-plane deformation disclosed by Feng et al. The provision of the cavity ensures that the cardiomyocyte movement can be facilitated in a relatively simple manner, thereby reducing the cost of the device of the present invention compared to the devices available in the art.

Due to the fact that the portion extends over the cavity, the out-of-plane deformation of the portion may be triggered by applying an external force. This has the advantage that the device can also be used to train immature cardiomyocyte cells by physiological stretching of the cells during the out-of-plane deformation of the deformable layer, such that the maturing process of the live cardiomyocyte cells is accelerated. Furthermore cells can be overstretched, i.e. mimicking patho-physiological stress. In addition, contraction of the cardiomyocytes is still facilitated due to the fact that the stretchable nature of the deformable layer allows for an in-plane cardiomyocyte-induced stretching of the deformable layer, such that both cardiomyocyte stretching and contraction during diastole and systole respectively can be simulated with this device in a quantitative manner at the appropriate stretch-contraction cycle frequency.

Furthermore, it has surprisingly been found that the provision of the grooves triggers the alignment of cardiomyocytes deposited onto the surface of the deformable layer into the grooves in one direction, such that patterning of bio-adhesives such as fibronectin is not required to ensure proper alignment of cardiomyocytes onto the deformable layer. This is an important advantage as fibronectin patterns can be difficult to reproduce due to the fact that they have to be stamped or printed onto the deformable layer, which are complex and cumbersome procedures. This hampers large-scale production.

In the present invention, the alignment of the cardiomyocytes relative to the direction of deformation of the deformable layer is readily achieved by the provision of the pattern of grooves, with the cardiomyocytes spontaneously assembling into these grooves on the adhesive-coated surface of the deformable layer. Such grooves can be routinely formed in the deformable layer, e.g. an elastomer layer, such that this approach is much more suitable for large-scale production. Subsequently, the deformable layer may be simply coated with an adhesive molecule, e.g. fibronectin, to create the cell attachment coating with the grooves ensuring the assembly of the cardiomyocytes in a patterned fashion in a subsequent cell plating step.

It has been found that fibronectin-coated and grooved PDMS (polydimethylsiloxane) is particularly suitable for triggering this cardiomyocyte alignment effect although it is expected that other predominantly hydrophobic elastomers, e.g. alternative silicones or parylene, will have a similar effect on the cardiomyocytes. In addition, optimal alignment results in PDMS grooves are achieved if the grooves have a dimension lower than 200 microns, preferably lower than 50 microns and more preferably of about 20 micron depth and about 20 micron width. In a preferred embodiment, each of said grooves has a pair of side walls, each side wall forming a substantially perpendicular angle with the surface of the deformable layer. It has been experimentally determined that the provision of a sharp angle between the layer surface and the groove sidewall improves the alignment process of the cardiomyocytes into the adhesive-coated grooves.

In an embodiment, the portion has a circular shape, the grooves extend radially from the center of the portion to at least one region of the deformable layer covering the substrate and the multi-electrode structure comprises at least one spiral electrode. The radially aligned assembly of the cardiomyocytes can be used to periodically deform the deformable layer to induce synchronous aligned stretching and contraction of the cardiomyocyte cells. It has further been found that the shape of the electrodes has a direct effect on the actual flexibility of the deformable layer, with the one or more electrodes spiraling outwards from the center of the portion minimizing the resistance introduced by the electrodes to the out-of-plane deformation of the deformable layer. In other words, such spiraling electrodes provide the most flexible configuration for a device of the present invention having a circular portion. In case of multiple electrodes, these electrodes may be placed in an interdigitated or interwoven configuration to maximize the compactness of the electrode layout.

In an alternative embodiment, the deformable layer comprises opposite ends, wherein said portion is located along an axis extending between the opposite ends, said portion separating said opposite ends from each other. In this embodiment, the deformable layer may have a so-called dog bone shape, which is characterized by two end portions interconnected by a relatively narrow middle portion in-between the two end portions. The middle portion is typically arranged over the substrate cavity. This arrangement has the advantage that the alignment of the grooves may be purposively chosen to promote stretching of the cardiomyocytes in a particular direction, i.e. along their main axis or in a transverse direction. To this end, the cell-alignment grooves may extend in a direction parallel or perpendicular to said axis.

Preferably, the multi-electrode arrangement comprises a plurality of electrodes that over said portion extend in a direction parallel to said axis, which has the advantage that the electrodes are not significantly stretched in their length direction when the deformable layer is deformed, thereby improving the robustness of the device. The end portions of the dog bone shaped deformable layer that attach the deformable layer to the substrate may have a predominantly semi-circular shape, which the electrode interconnects spiraling from the central portion of the dog bone shape towards the edges of the semi-circular end portions for reasons already given above.

In an embodiment, an edge of the deformable layer on the substrate comprises a tapered protrusion, said protrusion tapering inwards in a direction away from said portion; the substrate carries a bond pad; and the device further comprises an interconnection between the multi-electrode structure and the bond pad, said interconnection extending from the portion to the bond pad over the tapered protrusion. It has been found that this improves the robustness of the interconnect stack at the crossing point between the deformable layer and the substrate due to the fact that the angle between the deformable layer boundary and the substrate is reduced by these protrusions, thus reducing the risk of interconnect failure caused by the step from the deformable layer edge to the substrate.

The device of the present invention may be included in an assembly comprising a pressure chamber comprising a fluid inlet; wherein the portion forms a membrane over the pressure chamber; and a reservoir located over said portion, said pattern of grooves and the multi-electrode structure facing the reservoir. Such a device may be used for cardiotoxicity testing purposes by attaching cardiomyocytes to the upper part of the membrane and filling the reservoir with a composition including a compound under investigation, thereby exposing the cardiomyocytes to this composition, and monitoring the response of the cardiomyocytes to this exposure by recording the electrical activity, e.g. the field potential, of the cardiomyocytes during controlled stretch and relaxation.

In an embodiment, the fluid is a gas such as air, such that the out-of-plane deformation of the portion may be controlled by controlling the gas pressure inside the pressure chamber, thereby simulating the beating of the heart. This has the advantage that no fluid contact with the portion is required to invoke the out-of-plane deformation, thus reducing the risk of contamination or damage to the cardiomyocytes. In an alternative embodiment, the fluid is a liquid, and the deformable layer comprises the inlet. In this embodiment, any fluid placed in the container will envelop both surfaces of the stack such that the load of the fluid on the stack will effectively be zero. In this case, the out-of-plane deformation of the stack may be mechanically invoked.

In accordance with another aspect of the present invention, there is provided a method of manufacturing a device according to the present invention. This method has been designed with the emphasis on suitability for large scale production and reproducibility. In particular, it has been realized that the formation of the electrode arrangement on the deformable layer can be problematic as such layers tend to wrinkle or even delaminate when trying to process further layers on top of the deformable layer. Hence, in the method of the present invention, use has been made of the fact that several elastomer layers including PDMS can spontaneously adhere to a layer onto which the deformable layer is formed by forming the interconnect stack on the substrate and depositing the deformable layer over the interconnect stack, thereby avoiding the aforementioned processing problems.

In a first embodiment, the method of the present invention comprises providing a substrate; providing a patterned mask on the backside of the substrate; providing an etch stop layer on the front side of the substrate; forming an interconnect structure including a bond pad and an electrode arrangement on the etch stop layer; forming sacrificial portions in between the electrode arrangement; covering the resultant structure on the front side of the substrate with a deformable layer; providing a patterned etch protection layer over the deformable layer, said pattern exposing a region of the deformable layer over the bond pad; etching the exposed deformable layer to expose said bond pad; etching the exposed backside of the substrate to form the cavity, said etching terminating on the etch stop layer; removing the patterned etch protection layer and the etch stop layer; and removing the sacrificial portions through said cavity to define the grooves in the portion of the deformable layer.

In this embodiment, the grooves are defined in the deformable layer using portions of a sacrificial material, e.g. an etch mask material.

In a second embodiment, the method of the present invention comprises providing a substrate; providing a patterned mask on the backside of the substrate; providing an etch stop layer on the front side of the substrate; forming a interconnect structure including a bond pad and an electrode arrangement on the etch stop layer; removing the etch stop layer in between the electrode arrangement; etching groove regions in between the electrode arrangement; lining the groove regions with etch stop layer portions; covering the resultant structure on the front side of the substrate with a deformable layer; providing a patterned etch protection layer over the deformable layer, said pattern exposing a region of the deformable layer over the bond pad; etching the exposed deformable layer to expose said bond pad; etching the exposed backside of the substrate to form the cavity, said etching terminating on the etch stop layer; and removing the patterned etch protection layer and the etch stop layer.

In this embodiment, the grooves are defined by etching them into the substrate prior to the deposition of the deformable layer. Both embodiments address the same technical problem, namely how to provide well-defined patterns in a deformable material, in particular an elastomeric material and even more particularly in a PDMS layer, as it is known that well-defined patterns, especially patterns having sharp edges can only be formed using molding techniques. Hence, by providing the substrate with the desired groove shapes either in the form of portions of a sacrificial material or in the form of etched trenches or grooves, the deformable layer material can simply be deposited over these shapes without requiring any patterning of the deformable layer material.

Preferably, the method further comprises, prior to providing a patterned mask on the backside of the substrate, providing a patterned mask on the front side of the substrate, said patterned mask exposing an electrode region of the substrate; providing an etch protection layer on the backside of the substrate; etching a pyramid shaped recess in said electrode region; and removing the patterned mask and the etch protection layer. The provision of such pyramid shaped recesses facilitates the formation of pyramid shaped electrodes, which provide an improved contact with the composition in the reservoir of the aforementioned assembly.

The device resulting from the aforementioned embodiments of the method of present invention may be mounted on an interposer comprising a pressure chamber such that the portion of the deformable layer forms a membrane over the pressure chamber. In addition, an adhesive coating may be provided onto the grooved surface of the deformable layer, after which cardiomyocytes may be plated in culture medium onto the adhesive coating to initiate the spontaneous alignment of the cardiomyocytes in the grooves. This has the advantage that the cardiomyocytes can be applied to the deformable layer immediately prior to use, thereby ensuring that the cardiomyocytes are in a good condition during use. As such use may extend over prolonged periods of time, e.g. several weeks, the cardiomyocytes-containing culture medium may be applied e.g. 48 hours before use to allow for the completion of the spontaneous alignment. The device according to the present invention facilitates the in vitro read out of electrophysiological characteristics of the cultured cardiomyocytes. It can be envisioned that the device can be used for any assay wherein the electrophysiology of cardiomyocytes is of interest, e.g. cardiac development, phenotypic analysis of genetic disorders, analysis of stress conditions etc.

In accordance with another aspect of the present invention, there is provided a method of determining the electrophysiological response of cardiomyocytes to a compound, e.g. cardiotoxicity of a chemical compound, comprising providing the assembly of the present invention, providing the reservoir with a medium comprising the chemical compound to expose the cardiomyocytes to said compound; and measuring the response of the cardiomyocytes to said exposure.

The use of the assembly of the present invention in such a method provides an improvement in the accuracy of the cardiotoxicity determination of chemical compounds such as trial drugs.

BRIEF DESCRIPTION OF THE EMBODIMENTS

Embodiments of the invention are described in more detail and by way of non-limiting examples with reference to the accompanying drawings, wherein:

FIG. 1 schematically depicts a method of manufacturing a device for electrophysiology screening in accordance with an embodiment of the present invention;

FIGS. 2 and 3 schematically depict a top view of two different embodiments of a device electrophysiology screening as obtained by the method of FIG. 1;

FIG. 4 schematically depicts a method of manufacturing a device electrophysiology screening in accordance with another embodiment of the present invention;

FIGS. 5 and 6 schematically depict a top view of two different embodiments of a device for electrophysiology screening as obtained by the method of FIG. 4;

FIG. 7 schematically depicts the stretch modes of a cardiomyocyte;

FIG. 8 is a confocal microscopic image of with E 17,5 mouse cardiomyocytes cultured and aligned in a grooved PDMS substrate;

FIG. 9 schematically depicts a deformable circular membrane of a device in accordance with an embodiment of the present invention;

DETAILED DESCRIPTION OF THE DRAWINGS

Figure 1:
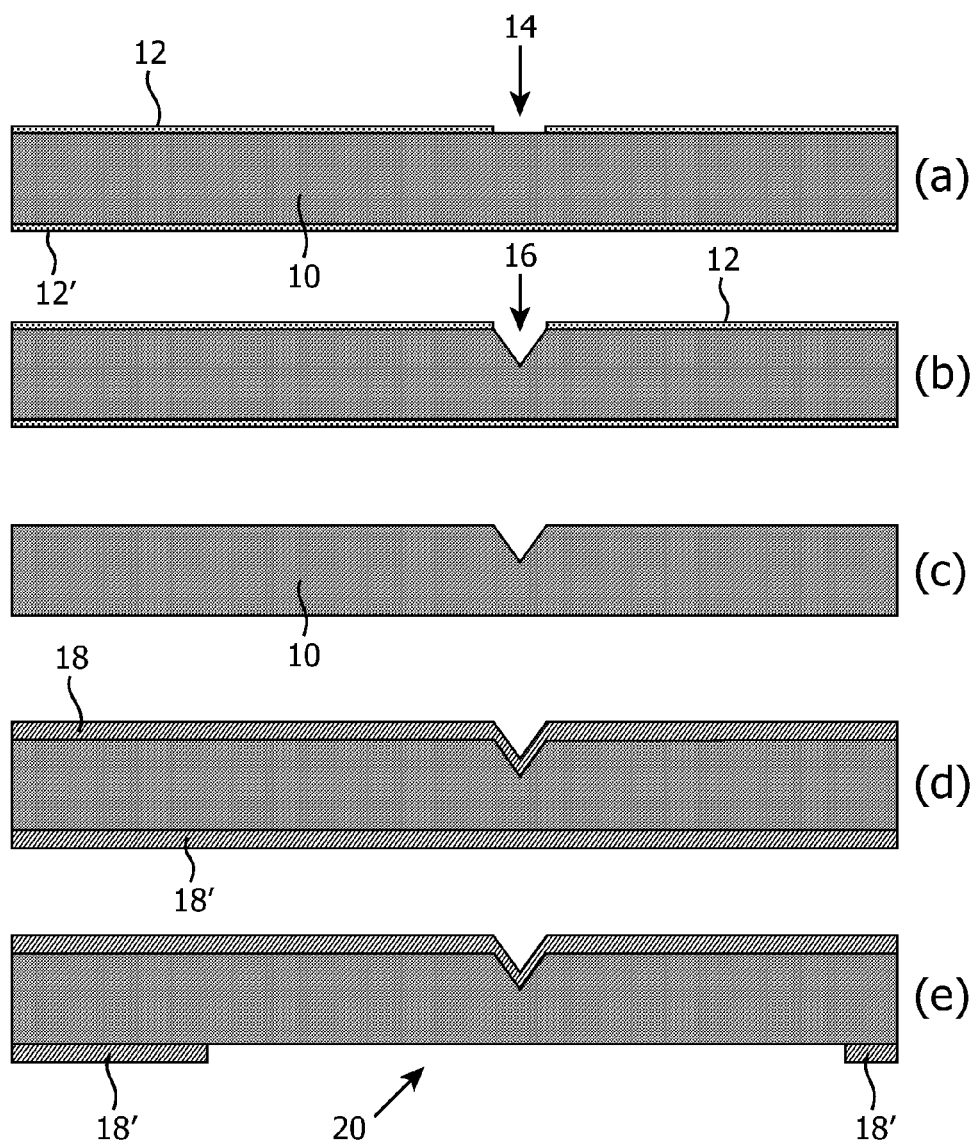
Figure 1:
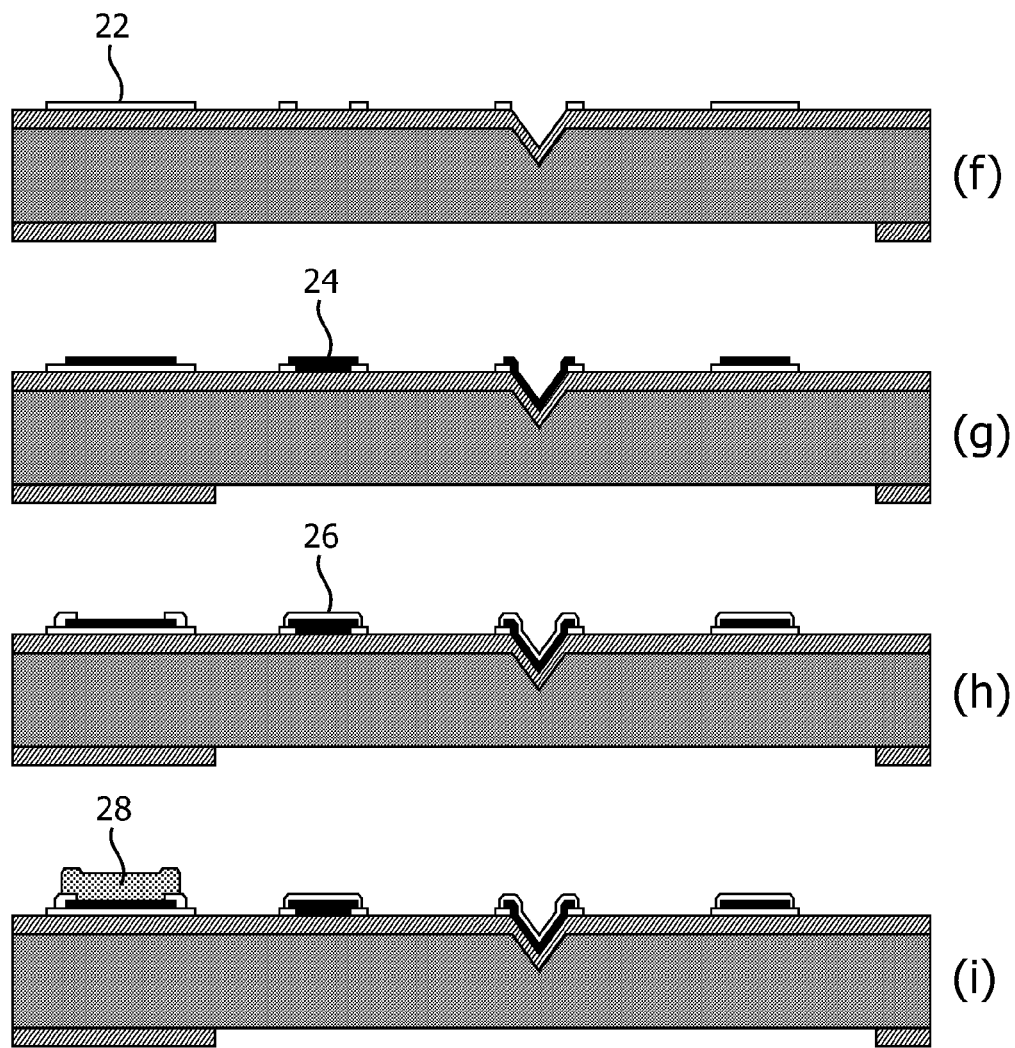
Figure 1:
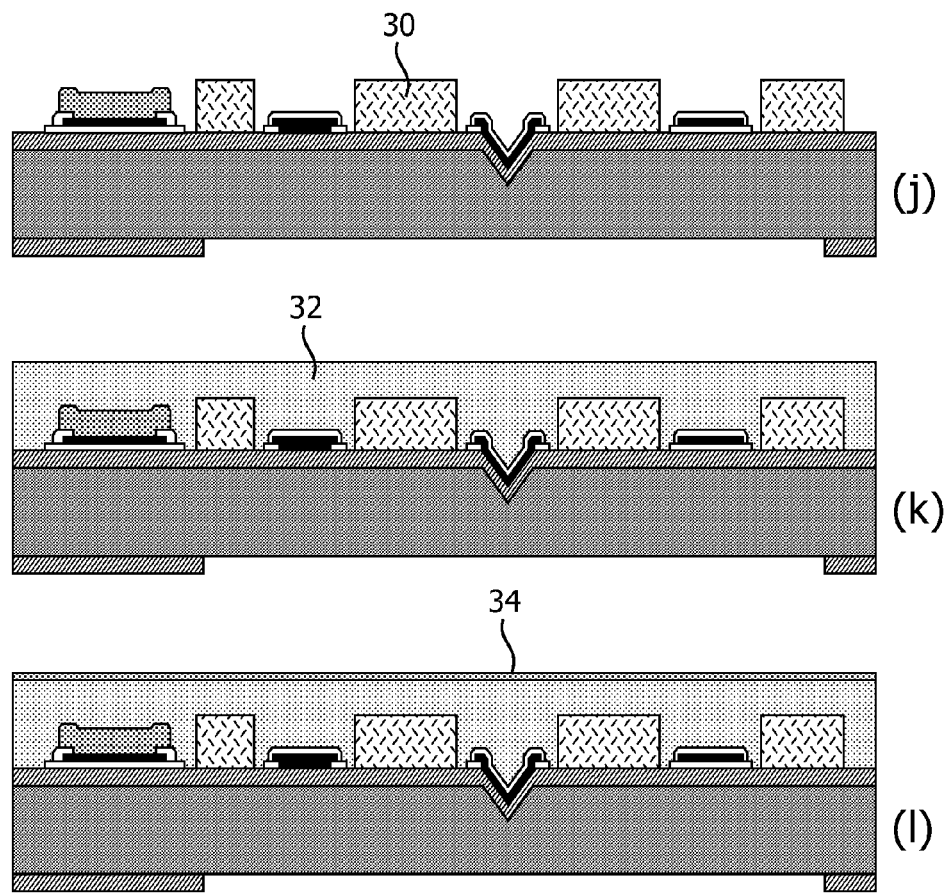
Figure 1:
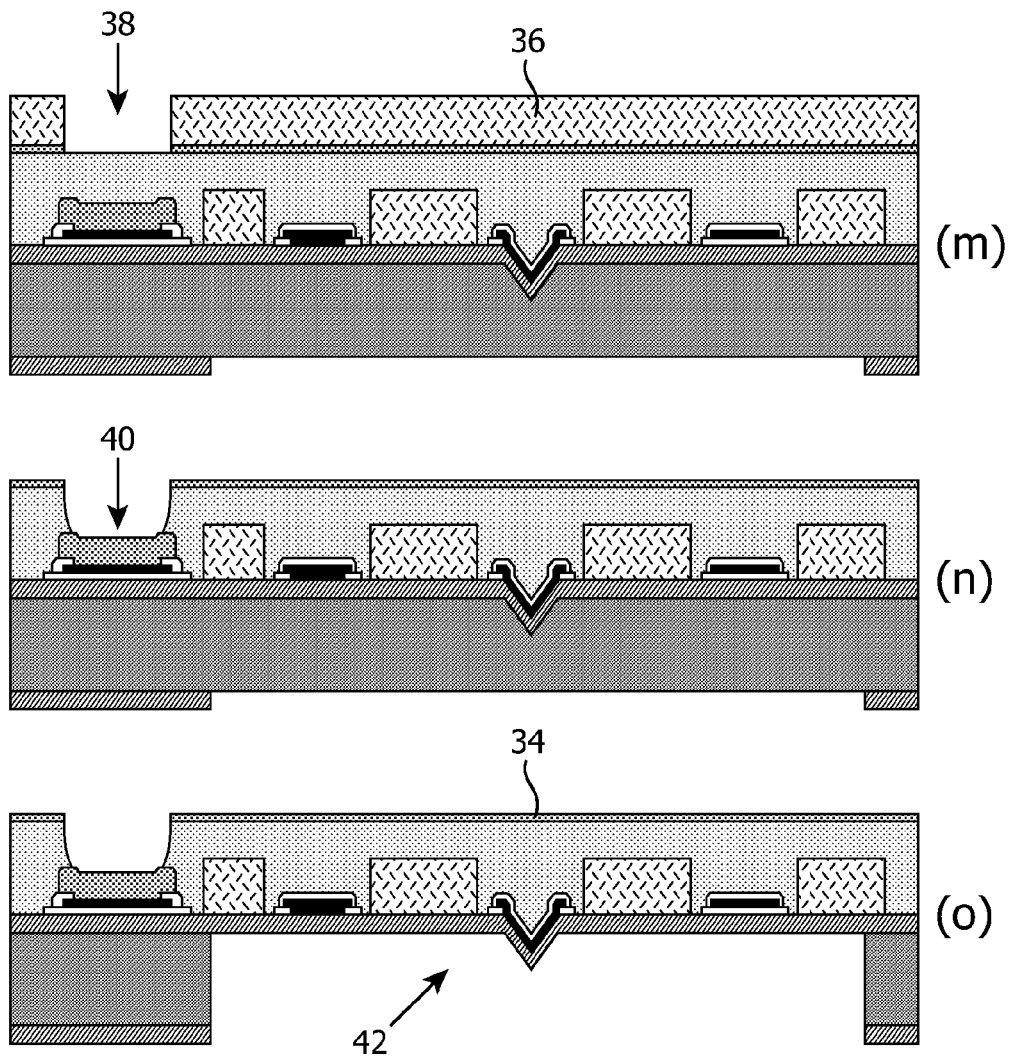
Figure 1:
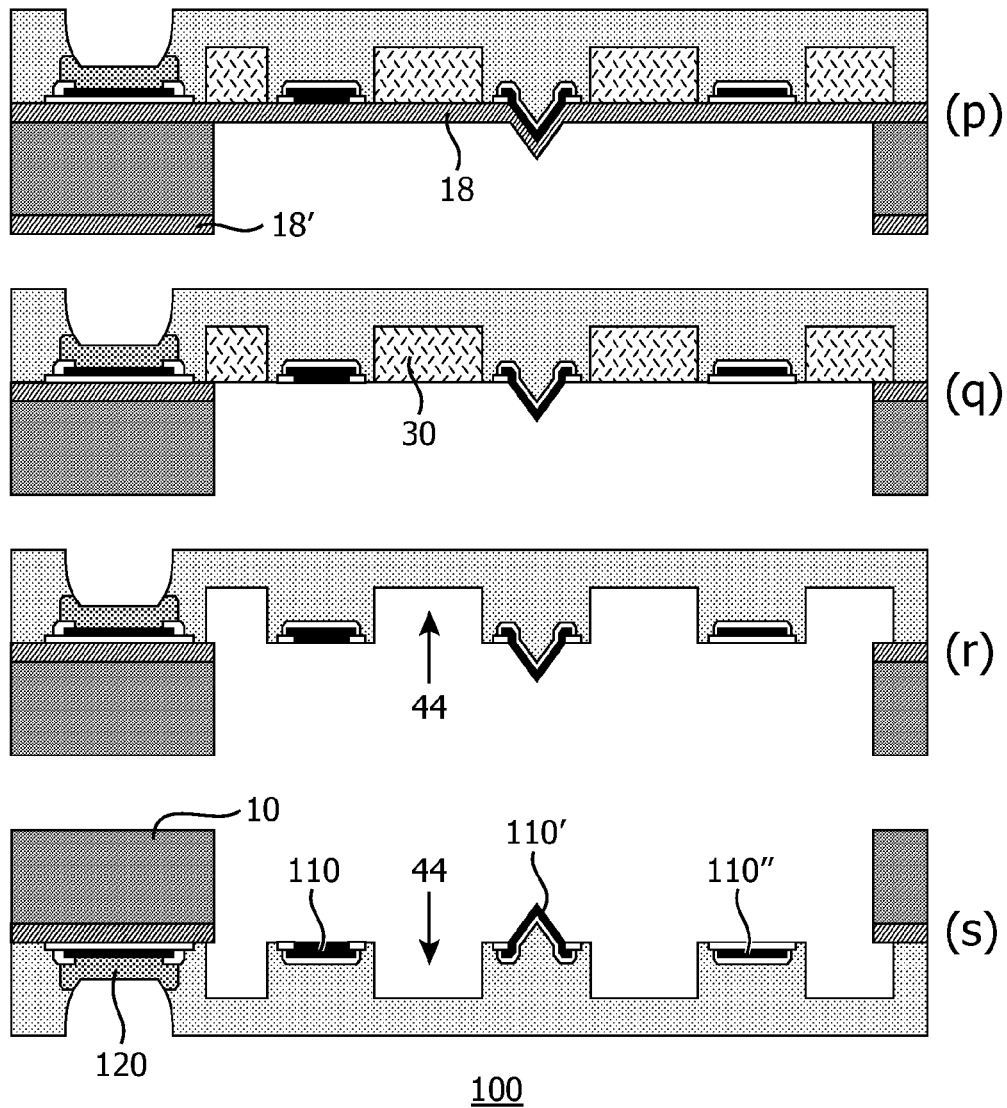
Figure 1:
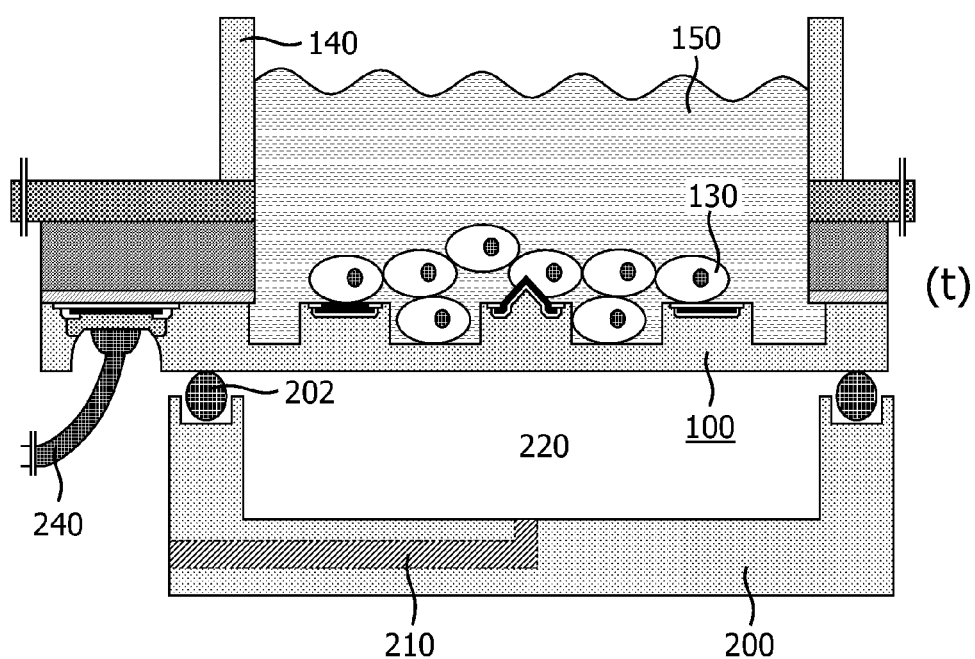

It should be understood that the Figures are merely schematic and are not drawn to scale. It should also be understood that the same reference numerals are used throughout the Figures to indicate the same or similar parts.

The device for electrophysiology screening of the present invention is based on the following general structural principle. An elastomer-based stack is mounted over a cavity in a substrate. This cavity effectively detaches a part of the elastomer-based stack from the substrate, such that the elastomeric nature of this part is facilitated to move out of the plane of the surface of the substrate. Several embodiments of such a device are contemplated, as will be discussed in more detail below.

In FIG. 1, a method of manufacturing a first embodiment of the device of the present invention is depicted.

In step (a), a substrate 10 preferably having a thickness of around 300-400 micron is supplied, which may be a silicon substrate or of another suitable substrate material. For the sake of brevity, the remainder of this description will assume that the substrate 10 is a silicon substrate by way of non-limiting example only. The back side of substrate 10 is provided with a suitable hard-etch mask 12', e.g. LPCVD grown silicon nitride ($Si_3N_4$). A further hard etch mask 12 is provided on the front side of the silicon substrate 10, which preferably is of the same material as the hard-etch mask 12'. In an embodiment, a single deposition step may be used resulting in the formation of hard etch mask 12' and further hard etch mask 12. The further hard etch mask 12 is patterned to define square openings 14 having dimensions of 10×10 micron or 20×20 micron by way of non-limiting example. Other suitable dimensions will be apparent to the skilled person.

In next step (b), the front side of the substrate 10 is exposed to an anisotropic etching step, e.g. using KOH to form pyramid-shaped recesses 16 in the substrate 10 in the location of the openings 14. The method proceeds to step (c) in which the hard etch masks 12 and 12' are removed from the substrate 10, e.g. using a wet etch. As suitable etch recipes are known per se to the skilled person, they have been omitted from the description for the sake of brevity. It is noted that the pyramid-shaped recesses form a template for pyramid-shaped electrodes, as will be explained in more detail later. However, it should be understood that such pyramid-shaped electrodes are entirely optional, and that steps (a)-(c) may be omitted without departing from the embodiment of the method of the present invention shown in FIG. 1.

In step (d), thermal oxide layers 18 and 18' are grown on the front side and back side of the substrate 10 respectively. The thermal oxide layers preferably have a thickness of around 1 micron. The thermal oxide layer 18' will act as an etch mask and the thermal oxide layer 18 will act as an etch stop layer in a subsequent process step (vide infra). In step (e), the thermal oxide layer 18' is patterned, e.g. by etching, to define the size and shape of the cavity to be formed in the substrate 10. This also defines the size and shape of the portion of the deformable layer to be formed that acts as the membrane covering the cavity in the substrate 10.

In steps (f)-(i) the interconnect structures including the electrodes and the bondpads are fabricated. First, a patterned lower isolating layer 22 is provided in step (f), followed by the addition of respective conductor portions 24 on the patterned lower isolating layer 22 in step (g), which are subsequently covered by an upper isolating layer 26 in step (h). By way of non-limiting example, parylene may be used for the lower and upper isolating layers 22, 26 and TiN may be used as the conductor material 24. Parylene is a particularly suitable insulating material because it is biocompatible, not brittle and stretchable to a certain extent. TiN is particularly suitable because it is commonly used as an electrode material with good results and because it has a good adhesion to other layers.

However, it should be understood that other materials may also be used. For instance, silicon nitride or oxide layers may be used for the isolating layers 22, 26 and other metals such as gold or platinum may be used as the conductor material 24. In an embodiment, Ti or Au are used the conducting material because it has been shown that thin titanium and gold layers can be stretched up to 100%, thus allowing the conductive pattern to be stretched without damage. It is further noted that for the interconnect structures acting as electrodes, the lower isolating layer was removed prior to forming the electrode, e.g. by a selective etching step.

In step (i), a bonding layer 28 is deposited on top of the parts of the interconnect structure that define bond pads. For instance, the bond pads may be provided with a 1 micron thick layer of Al(Si/Cu). The bonding layer 28 is typically required when TiN is used as the conducting material 24, because TiN is not bondable. It will be immediately apparent to the skilled person that step (i) may be omitted if a conducting material 24 is used that can be directly bonded to.

In step (j), a sacrificial layer 30 such as a resist layer is deposited and patterned in the shape of the grooves to be formed in the membrane portion of the deformable layer. The sacrificial layer 30 may have a thickness of around 10-20 micron. The resulting structure is covered in a layer of the deformable material 32 preferably having a thickness of around 25 micron, as shown in step (k). The deformable material preferably is an elastomer, and more preferably is PDMS. PDMS may be spin-coated onto the structure resulting after step (j) and subsequently cured at a suitable temperature, e.g. 90° C.

In step (l), a thin layer 34 of aluminum, e.g. 30-50 nm thick is formed over the surface of the deformable layer 32, e.g. by sputtering of evaporation to provide an inert layer over the deformable layer 32. This is particularly relevant if the deformable layer 32 is a PDMS layer as PDMS has a tendency to readily adhere to other surfaces, such as the surfaces of the vacuum and electrostatic chucks in the processing equipment. The thin layer 34 is subsequently covered with a mask layer 36. Next, in the location 38 of the bond pads, the mask layer 36 and the inert layer 34 is opened in step (m) and the deformable layer 32 is opened in step (n) to provide access to the bond pads. The mask layer 36 may also be removed in step (n). The deformable layer 32 may be opened using any suitable etch recipe, e.g. by means of reactive ion etching.

In step (o), the wafer is flipped (not shown) and the cavity 40 is formed by etching away the substrate 10 until the etch stop layer 18 has been reached. In a preferred embodiment, the cavity 40 is formed using the Bosch process, which is a dry etching process. Alternatively, the cavity 40 may be formed by wet-etching the exposed back side of the substrate 10 using any suitable recipe, such as the $HF/HNO_3/$ acetic acid (HNA) etch recipe by way of non-limiting example although care has to be taken with the HNA recipe not to damage the etch stop layers and subsequently attack the front side of the wafer. Subsequently, as shown in step (p), the inert layer 34 is removed, followed by the removal of the etch stop layer 18 and mask layer 18' in step (q) and the sacrificial layer portions 30 in step (r). This may be achieved by a sequence of suitable wet etching steps. By removing the sacrificial layer portions 30, the grooves 44 in the deformable layer 32 are exposed, i.e. opened.

In case of a substrate 10 comprising multiple cavities 42, e.g. in case of the substrate 10 being a wafer, the wafer may now be diced into the individual devices 100.

In step (s), the device 100 is flipped. By way of non-limiting example, the device is shown to have a bond pad 120, electrodes 110 and 110' and an interconnect structure 110" separated by grooves 44 in the deformable layer 32. In step (t), an assembly may be formed by mounting the device 100 onto an interposer 200, which may include a seal 202 for establishing a fluid-tight connection between the interposer 200 and the device 100. This mounting may define a pressure chamber 220 to which at least the membrane portion of the deformable layer 32 acts as a lid, and to which a fluid such as a gas, e.g. air or a liquid may be provided via inlet 210.

An adhesive, preferably a bio-adhesive and more preferably fibronectin may be coated onto the grooved surface of the deformable layer 32, after which cardiomyocytes 130 may be plated, e.g. in cell culture medium 150 onto the coated surface of the deformable layer 32, leading to the spontaneous alignment of the cardiomyocytes 130 in the grooves 44 of the deformable layer 32. This plating can be performed immediately prior to use of the cardiomyocyte assembly on the device in case the cardiomyocytes 130 need to be as fresh as possible.

The cardiomyocyte alignment process is most effective if the deformable layer 32 is a PDMS layer, in which the side walls of the grooves 44 form a sharp angle, i.e. 90°, with the raised portions of the deformable layer 32. Preferably, the grooves 44 have a rectangular shape with a width and depth each selected from a range of 5-45 micron. More preferably, the grooves 44 have a square shape with width and depth each being 20 microns. Another reason why PDMS is a particularly suitable material is because it is bio-compatible and can be elongated up to 100%.

A container structure 140 is adhered, e.g. glued, to the deformable layer 32 to define a reservoir over its grooved membrane portion. The container structure 140 may for instance be a glass or plastic ring, or any other suitable structure. The reservoir may be filled with culture medium. In a preferred embodiment, a compound of which the cardiotoxicity is to be tested can be added at any point, e.g. may be added after the culture medium has been placed in the reservoir. The bond pad 120 is connected to a lead 240 which connects the bond pad to external circuitry (not shown), such as a printed circuit board. Other suitable assembly arrangements will be apparent to the skilled person.

In operation, i.e. after the cardiomyocytes 130 have aligned with the grooves 44, the reservoir may be filled with a solution 150. The solution 150 covering the cardiomyocytes 130 may be the aforementioned culture medium, a Tyrode solution, a standard buffer for electrophysiology or standard nutrient solution for cell culture, i.e. a so-called culture medium, and may contain varying concentrations of molecules, e.g. electrolytes such as potassium, sodium and calcium, amino acids, proteins and chemicals (for example hypertrophy and or oxidate stress inducing compounds). In addition, the pH and atmospheric conditions might be varied to simulate different (patho-)physiological conditions known in vivo, such as conditions induced by strenuous exercise characterized by for example a decrease in pH, increase in potassium concentration, reduced $O_2$ concentration, and so on.

An experiment may start with a baseline measurement, after which a chemical compound of interest may be added to the solution 150. It is also envisioned that different types of cardiomyocytes, or different conditions are compared. During the experiment, cardiomyocyte responses, i.e. the response of the cardiomyocytes 130 to the exposure of interest can be monitored over time in a preferred embodiment, drug concentrations can be cumulatively increased to measure a dose-dependent response of the cardiomyocytes 130. In the context of the present invention, it should be understood that the phrase 'chemical compound' is not intended to be limited to compounds intended for use as a pharmaceutical or to single compounds only. In general, any substance, such as compound mixtures, emulsions and solutions comprising one or more compounds may be tested using the device of the present invention.

The pressure in the pressure chamber 220 may be regulated, e.g. reduced or increased by withdrawing or adding a gas such as air via the inlet 210. This forces the grooved portion of the deformable layer 32 to stretch in a direction out of the plane of the substrate 10, e.g. away from the reservoir when reducing the pressure in the pressure chamber 220 or into the reservoir when increasing the pressure in the pressure chamber 220. Consequently, the live cardiomyocyte cells assembled onto the grooved portion of the deformable layer 32 are also stretched in this process. In addition, the autonomous contraction of the cardiomyocytes triggers an in-plane deformation of the grooved portion of the deformable layer 32, which comprises a thickening (contraction) of the grooved portion of the deformable layer 32 underneath the cardiomyocytes 130 and a thinning (stretching) of the grooved portion of the deformable layer 32 outside the area in which the cardiomyocytes are located.

The fact that the assembly as shown in FIG. 1(*t*) has a grooved deformable layer 32 has two main advantages. Firstly, repetitive stretching may be applied to immature cardiomyocytes, e.g. derived from a source of stem cells to further mature these cells into mature cardiomyocytes. This ensures that the device comprises fully matured cardiomyocytes, which improves the relevance of the clinical data obtained with this device. It also provides the opportunity to measure the electrophysiological changes of the cells during the maturation process.

Secondly, the deformable layer 32 may be stretched synchronously with the contraction rhythm of the cardiomyocytes 130, with a frequency and force to be chosen within the (patho-)physiological range of the heart, to resemble the cardiomyocyte stretching which occurs in the beating heart. This for instance allows for the self-aligned cardiomyocytes 130 to be passively stretched to allow ion channel measurements (by recording the field potential) in a dynamic cardiomyocyte model system mimicking the heart at rest and under controlled (patho)-physiological stress. The cardiomyocyte contraction rhythm may be autonomous or electrically induced, with a chosen frequency.

Figure 2:
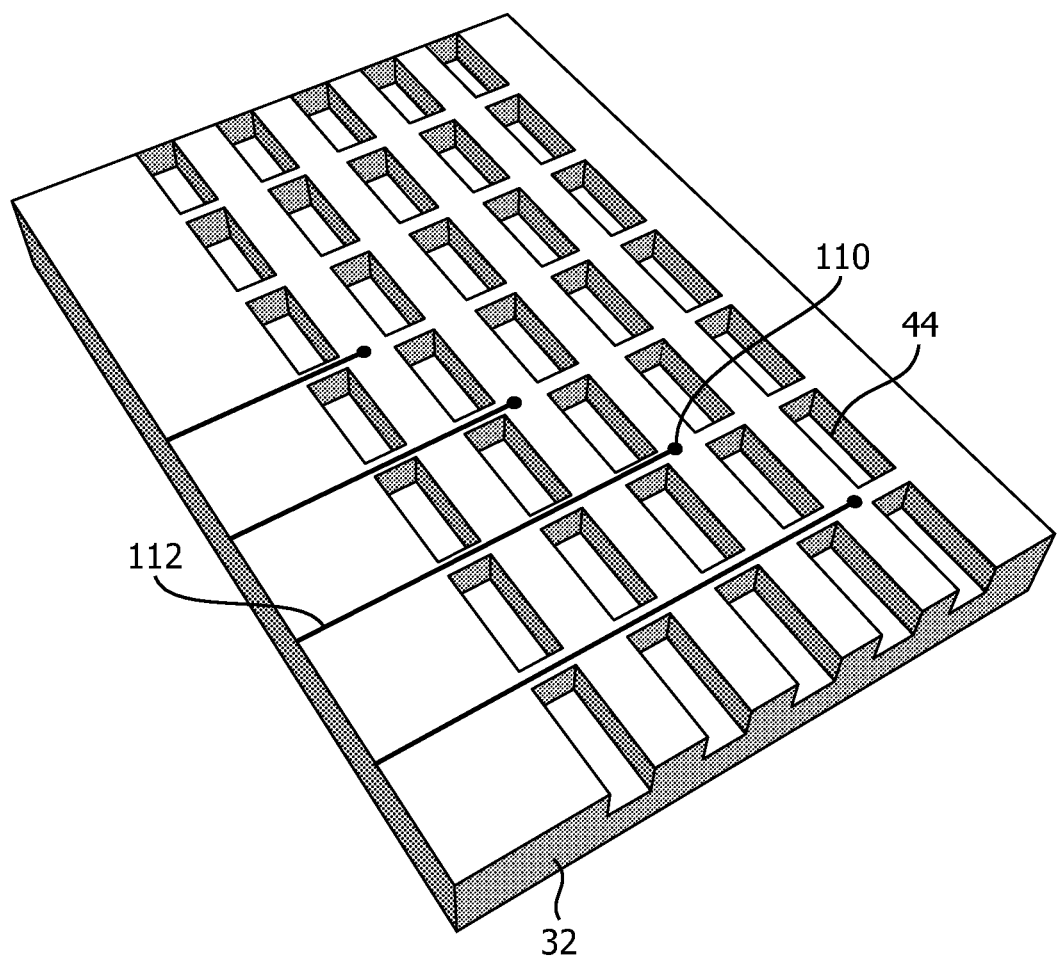

It is shown in FIG. 2 that when following the method depicted in FIG. 1, the grooves 44 in the deformable layer 32 may have to be interrupted in the location of the electrodes 110 and associated interconnects 112. This is in particular relevant for devices in which the membrane is circularly shaped. In other words, the electrodes 110 and associated interconnects 112 are located on the ridges separating the grooves 44. When plating the cardiomyocytes 130 over the membrane portion of the deformable layer 32, covering of these ridges by the cardiomyocytes 130 cannot be avoided, although the vast majority of the cardiomyocytes 130 will spontaneously align in the grooves 44. Consequently, the vast majority of the cardiomyocytes 130 will lie in an aligned and interconnected fashion in the grooves 44, such that meaningful readings from the coordinated stretch/contraction cycles of the cardiomyocytes 130 can still be obtained.

Figure 3:
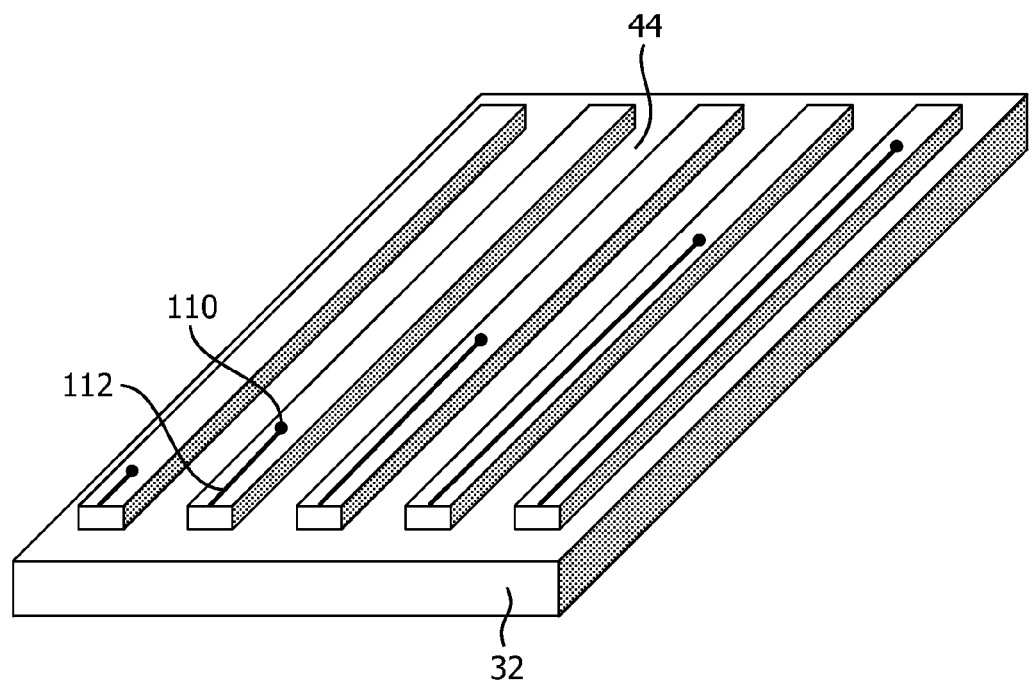

FIG. 3 depicts an alternative embodiment of the device obtained by following the method of FIG. 1, in which the membrane has a rectangular shape. In this embodiment, the grooves 44 may extend over the full length of the deformable layer 32, in which case the interconnects 112 of the electrodes 110 run parallel to said grooves 44 over the ridges separating the grooves 44.

Figure 4:
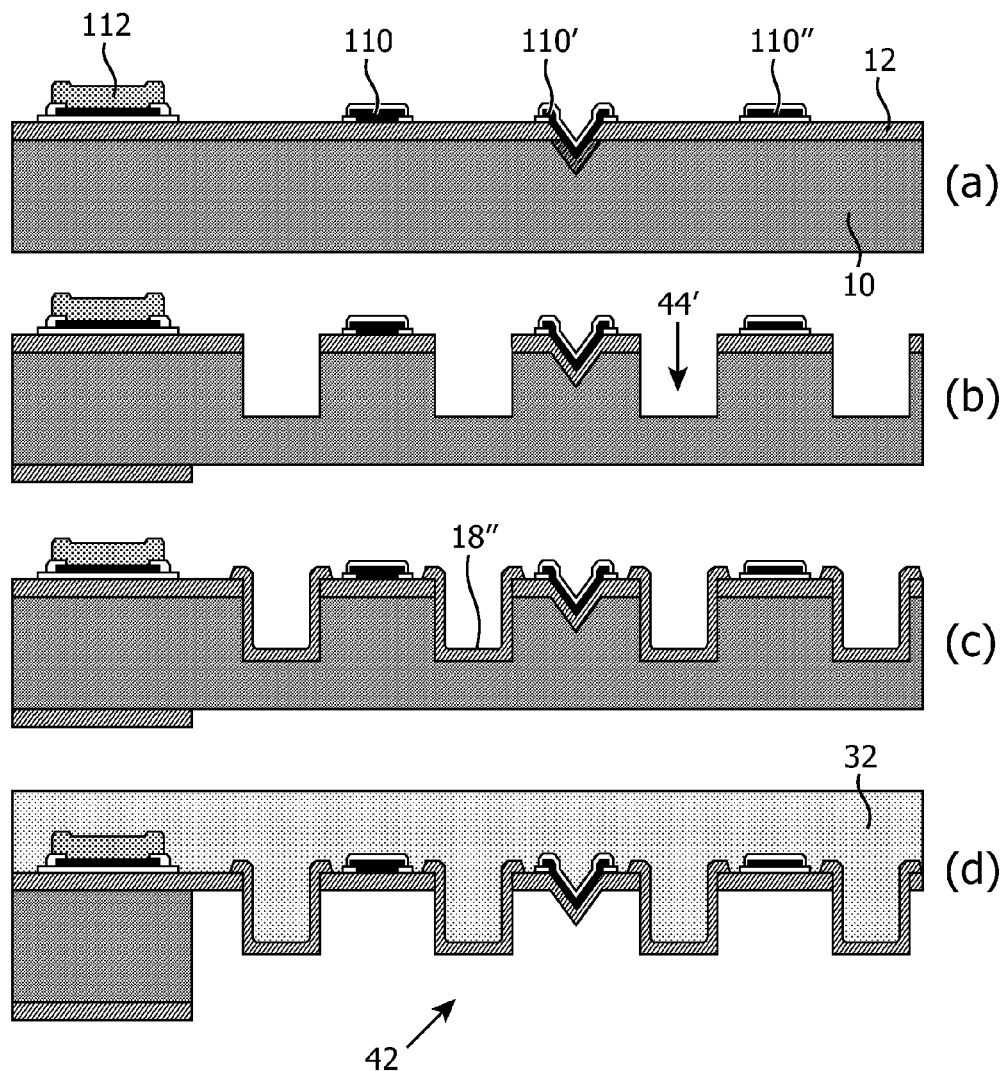
Figure 4:
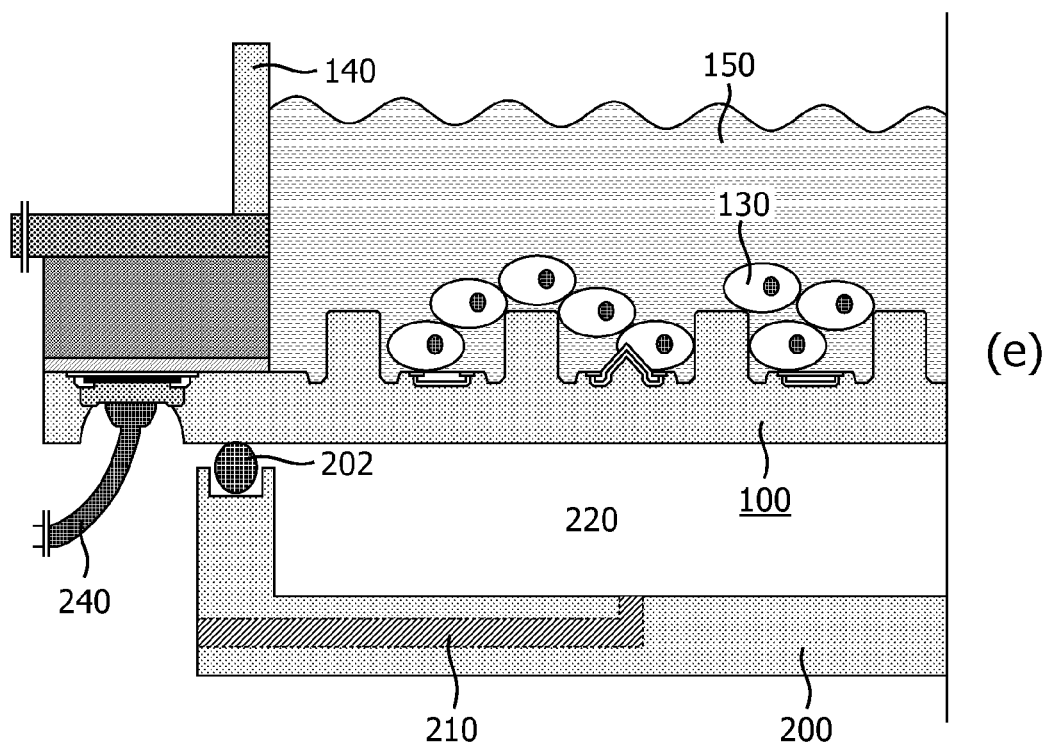

FIG. 4 shows an alternative embodiment of the method of the present invention, in which the electrodes 110 are formed in the grooves 44. This alternative embodiment may follow steps (a)-(i) as shown in FIG. 1, thus providing the resultant structure as shown in FIG. 4(a). It is reiterated that steps (a)-(c) of FIG. 1 are optional, as previously explained.

In step (b) of FIG. 4, the etch stop layer 12, which as previously indicated may be a LPCVD deposited $Si_3N_4$ layer or may be a thermal oxide layer, is opened in selected locations between the various interconnect structures. A suitable etching step, e.g. a RIE step, is subsequently performed to define the outline of the ridges 44' that separate the grooves 44 to be formed. In step (c), the outline of the ridges 44' is lined with the portions 18" of the etch stop layer material also used for etch stop layer 18, such that a continuous etch stop layer is once again formed over the front side of the substrate 10. The method may now proceed as previously described in steps (k)-(s) of FIG. 1, including the deposition of the deformable layer 32 and creation of the cavity 42 as also shown in FIG. 4(d). FIG. 4(e) depicts the resulting assembly. It is noted that contrary to the assembly in FIG. 1(t), the electrodes 110, 110' and the interconnect structures 110" are now formed in the grooves 44 of the device 100.

Figure 5:
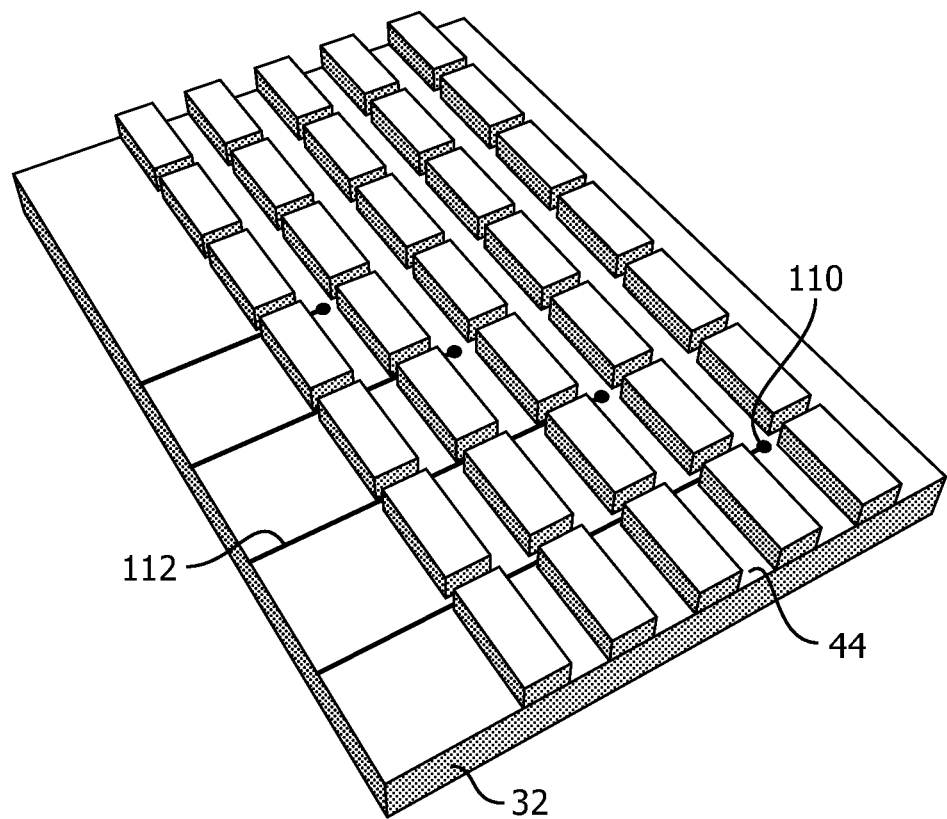

The method depicted with the aid of FIG. 4 has the advantage that the grooves 44 do not need to be interrupted by ridges 44', because the electrodes 110 and associated interconnects 112 are also formed in the grooves 44, as shown in FIG. 5.

Figure 6:
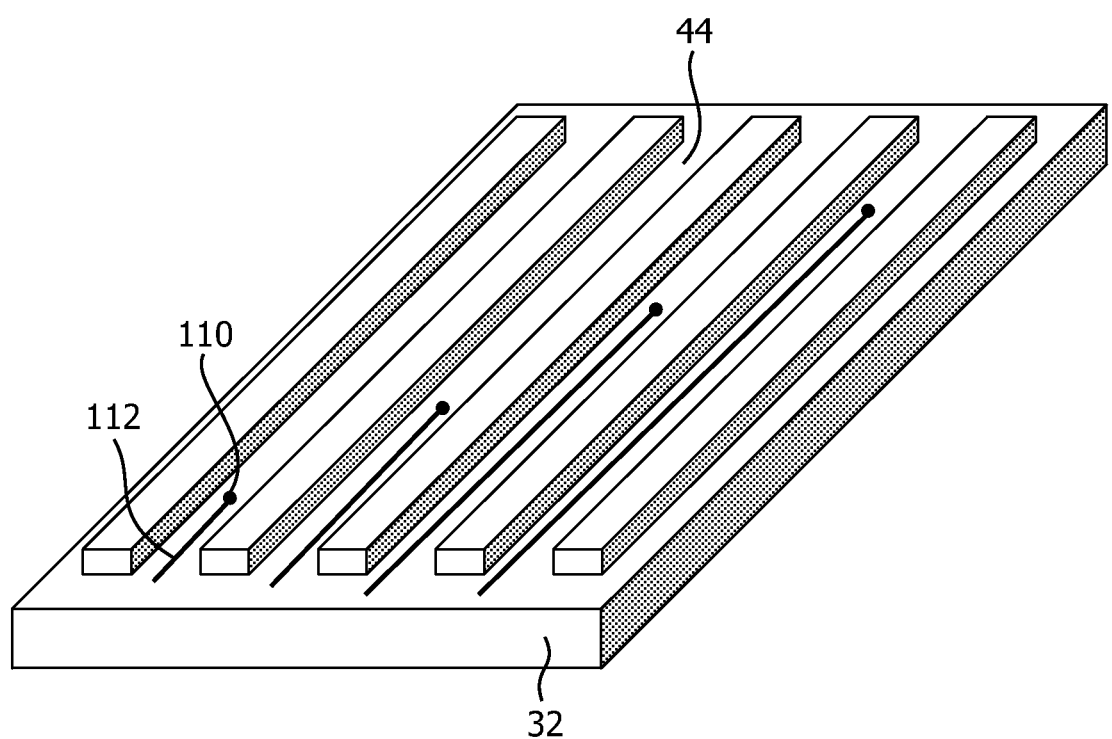

As shown in FIG. 6, which depicts an alternative embodiment of a device obtained by the method of FIG. 4, the ridges themselves do not need to be interrupted either when the electrodes 110 and interconnects 112 are formed in the grooves 44.

Figure 7:
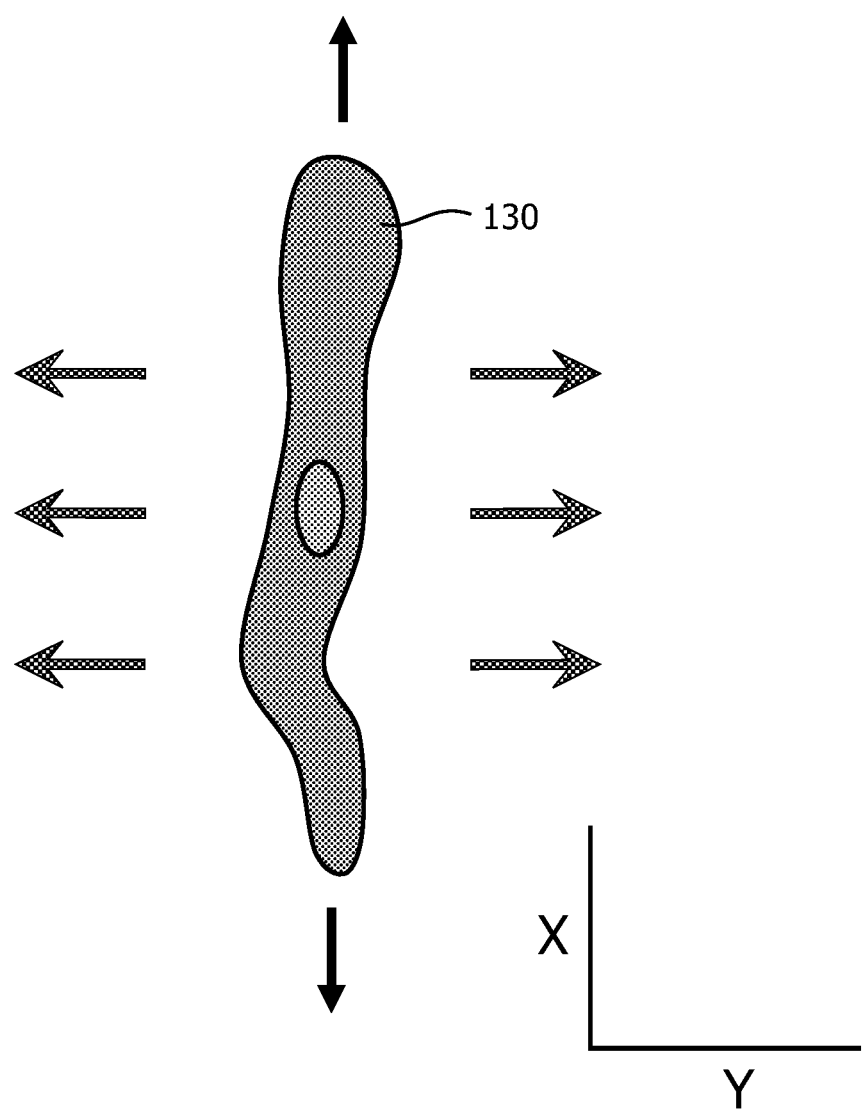
Figure 8:
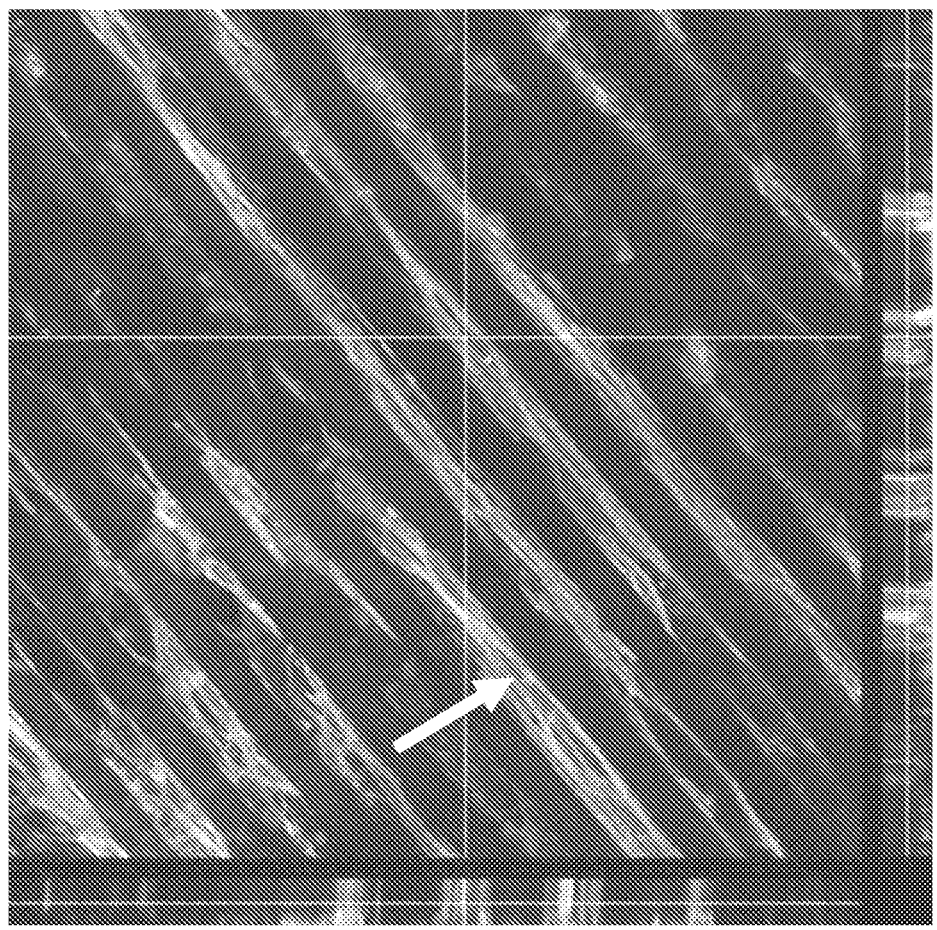

FIG. 7 schematically shows a cardiomyocyte 130, which may be stretched in the direction of its main axis, i.e. along the x-axis, or transverse to its main axis, i.e. along the y-axis. These different stretch modes can be used to achieve different types of cell differentiation/maturation when training the cells. FIG. 8 provides experimental evidence of the ability of the cardiomyocytes 130 to spontaneously align in an elastomeric grooved layer 32 coated with fibronectin. The white arrow indicates aligned E17,5 mouse cardiomyocytes on a grooved PDMS substrate. The cardiomyocytes were stained with DAPI, α-actin and phalloidin for better detectability under the confocal microscope used to generate the image shown in FIG. 8.

Figure 9:
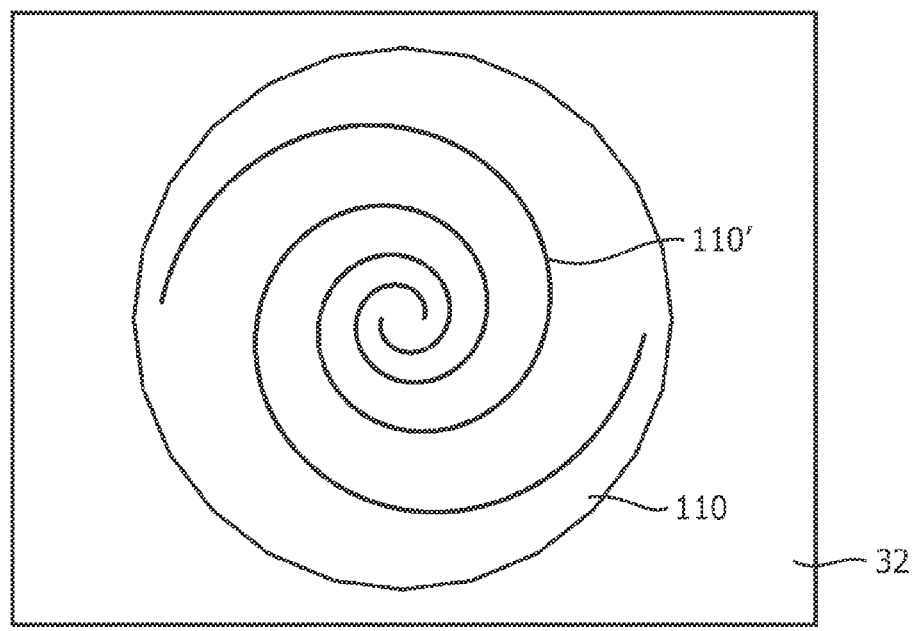

The membrane portion of the deformable layer 32 may have any suitable shape. For instance, in the top view of FIG. 9, the membrane portion has a circular shape which carries spiraling electrodes 110 and 110'. The pattern of grooves (not shown) extends radially from the centre of the membrane portion towards the edge of the membrane portion, i.e. towards the part of the deformable layer 32 attached to the substrate 10. Although spiraling electrodes require more are than meandering or radially extending electrodes, e.g. electrodes running parallel to the radially extending grooves, it has been found that meandering or radially extending electrodes result in a substantial stiffening of the deformable layer 32 as the stretching tolerance in such electrodes in practice is limited to 10-20% of their length. In addition, meandering or radially extending electrodes cause a substantial strain on the interconnect structure during the stretch cycles of the deformable layer 32, thereby acceleration device failure through interconnect fatigue.

Figure 10:
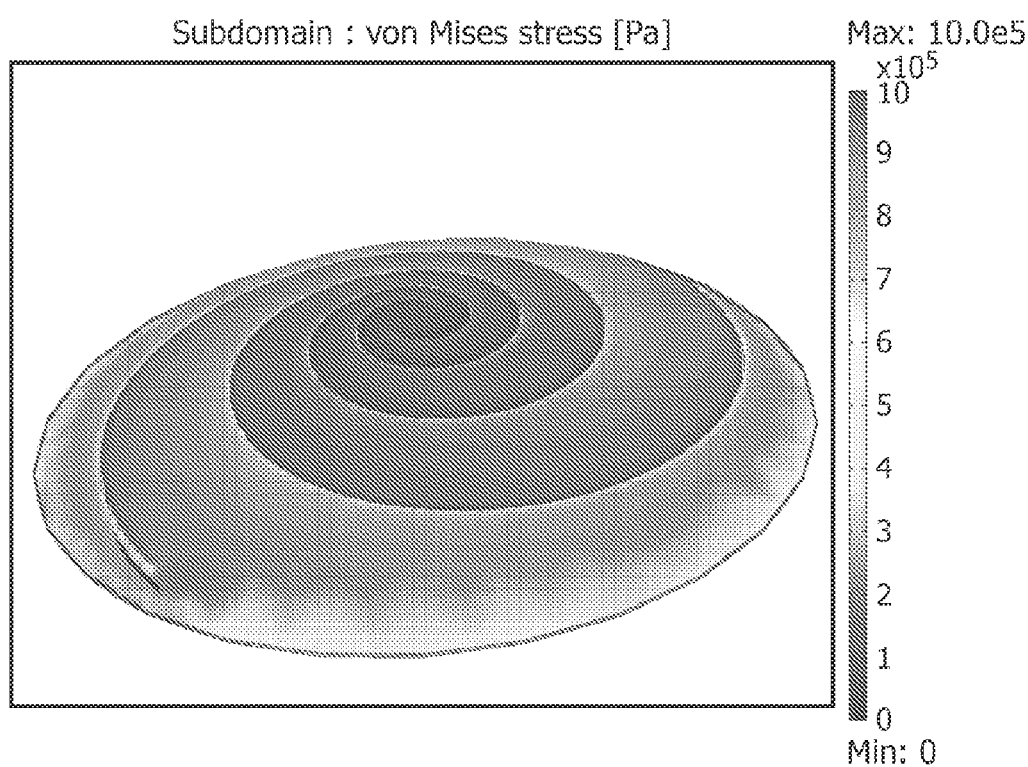
FIG. 10 shows a stress test simulation result of the membrane of FIG. 9.

In contrast, spiral-shaped electrodes provide an increased flexibility to the deformable layer 32. This is demonstrated in the top view of FIG. 10, in which the simulation results of mechanical stress test of the device of FIG. 9 when a back pressure is applied to the membrane portion. An imaginary radial line can be drawn from the centre of the membrane portion to its edge. When following this line, it will cross the spiraled interconnect structure several times while the crossings themselves are connected only to the highly flexible elastomer, e.g. PDMS, with the crossing portions of spiraled interconnect structure being stretched predominantly in their width direction. Consequently, the membrane itself is highly flexible whilst the stress in the interconnect structure remains very low as indicated by the simulation result in FIG. 10.

Figure 11:
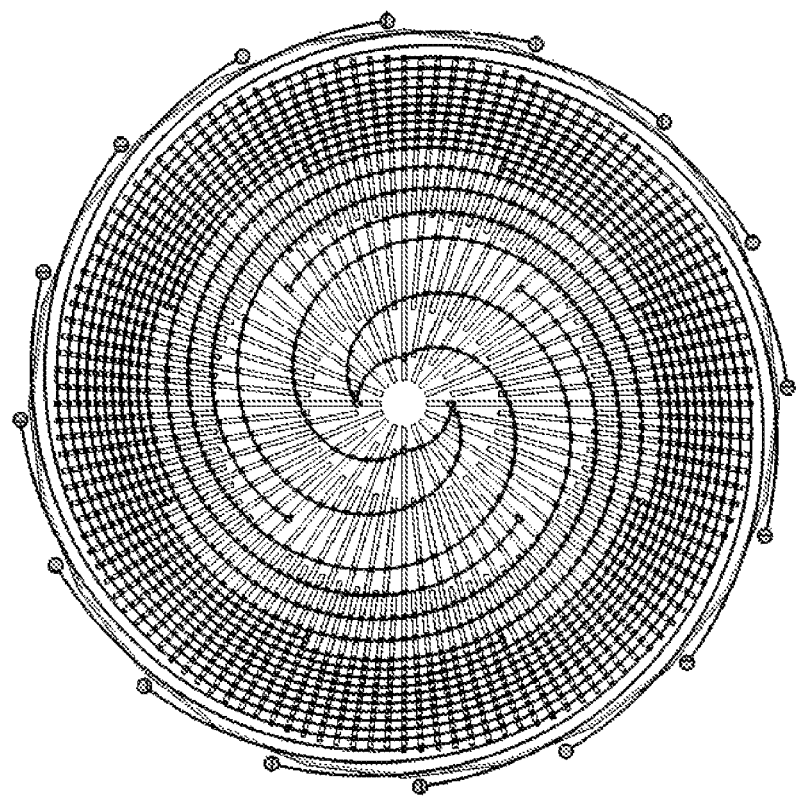
FIG. 11 shows another circular membrane of a device in accordance with an embodiment of the present invention in further detail.

FIG. 11 depicts a real device 100 comprising 16 spiraling electrodes and radial alignment grooves. In a device 100 having a circular membrane portion, such as the device shown in FIG. 11, the alignment grooves extend radially from the centre to the edge of the membrane, as previously explained. Consequently, the aligned cardiomyocytes are simultaneously subjected to an isotropic stretch force, i.e. a force of similar magnitude in the direction of their main axis as well as transverse to their main axis, when applying an external pressure to the membrane, e.g. by pressurizing the pressure chamber 220 in the assembly of e.g. FIG. 1(t), which typically expands a circular membrane into a dome shape.

Figure 12:
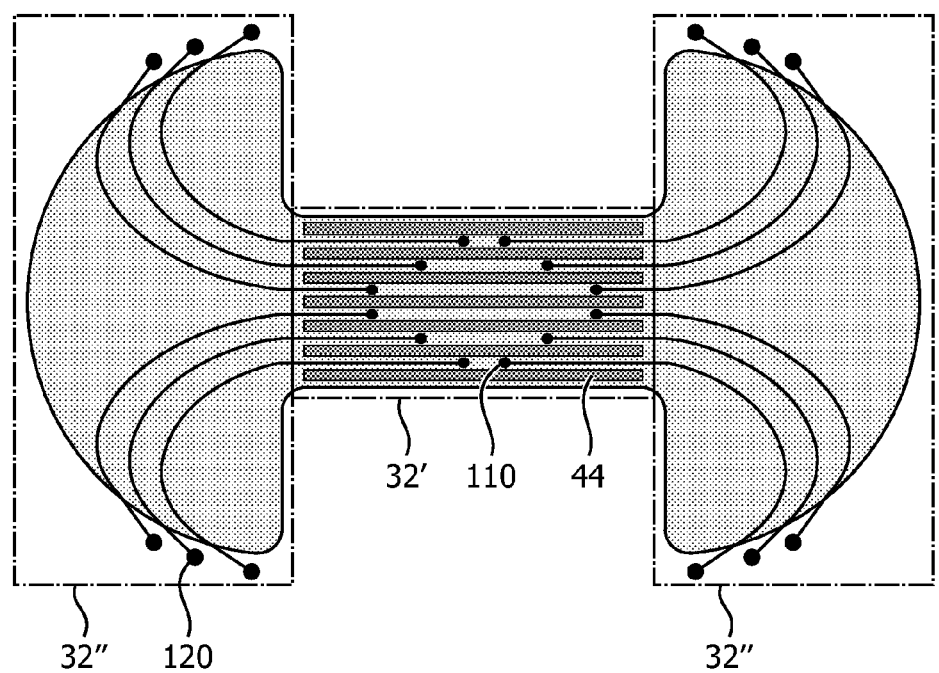
FIG. 12 shows a dog bone-shaped deformable layer of a device in accordance with another embodiment of the present invention.

However, as previously explained, it may be desirable to subject the cardiomyocytes 130 to a stretch force along or transverse to their main axis only. This may be achieved by changing the shape of the membrane portion of the deformable layer 32, i.e. the portion that covers the cavity, and the underlying cavity 42. A top view of an example of a device 100 having such a suitable shape is shown in FIG. 12. Here, the deformable layer 32 has a so-called dog bone shape in which end portions 32" are attached to the underlying substrate 10 and separated from each other by the membrane portion 32' covering the underlying cavity 42. The grooves 44 run parallel to the imaginary horizontal axis extending between the two end portions 32" through the membrane portion 32'.

When exposed to a pressure from the pressure chamber 220, the dimensions of the membrane portion 32' are such that it will adopt a cylindrical shape. Hence, the membrane portion 32' is stretched in a direction transverse to the imaginary horizontal axis, and consequently, the cardiomyocytes 130 that are aligned with the grooves 44 such that their principal axis is aligned with the imaginary axis are stretched in a direction transverse to their principal axis. To achieve the cylindrical deformation of the membrane portion 32', the membrane portion 32' may have a rectangular shape with its longer side running parallel to the imaginary horizontal axis extending between the two end portions 32" through the membrane portion 32'.

The electrodes 110 and their interconnects should preferably run parallel to this imaginary horizontal axis over the membrane portion 32', either adjacent to or inside the grooves 44 depending on which of the manufacturing methods of the present invention has been used. This ensures that the electrodes and their interconnects are not significantly stretched in their length direction as the main deformation of the membrane portion 32' is in the transverse direction, as previously explained. Hence, this increases the lifetime of the device 100 as the electrodes 110 and their interconnects are less prone to failure due to prolonged stretching.

The end portions 32" of the deformable layer 32 may have any suitable shape. In FIG. 12, the end portions 32" have a semi-circular shape, with the metal interconnects spiraling outward from the edge of the membrane portion 32' to the bond pads 120. As previously explained, the spiral shape of the metal portions on the deformable layer 32 ensures that the stress experienced by these metal portions is significantly reduced compared to linear or meandering shapes. It should be understood that in the context of the present invention, a spiraling electrode or interconnect may have a shape that is curved in accordance with mathematical equations defining spiral or helix shapes. However, as will be apparent, the electrode or interconnect may comprise less than a single pitch of the spiral or helix shape.

Figure 13:
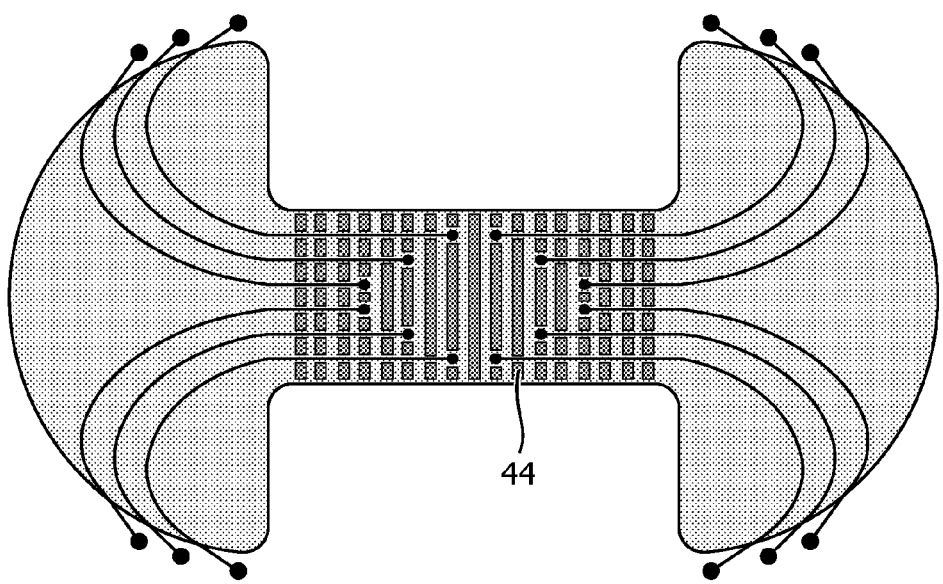
FIG. 13 shows a dog bone-shaped deformable layer of a device in accordance with yet another embodiment of the present invention.

The device shown in FIG. 12 facilitates exposing cardiomyocytes 130 to a stretch mode that is predominantly in a direction that is transverse to their principal axis. However, by aligning the grooves 44 in a direction that is substantially perpendicular to the imaginary horizontal axis extending between the two end portions 32" through the membrane portion 32', the cardiomyocytes 130 will be subjected to a stretch mode that is predominantly in a direction in parallel with their principal axis. This is shown in FIG. 13. The grooves 44 may be interrupted as shown in FIG. 2 to allow the electrode interconnects to extend from the membrane portion 32' to the end portions 32" of the deformable layer 32.

Figure 14:
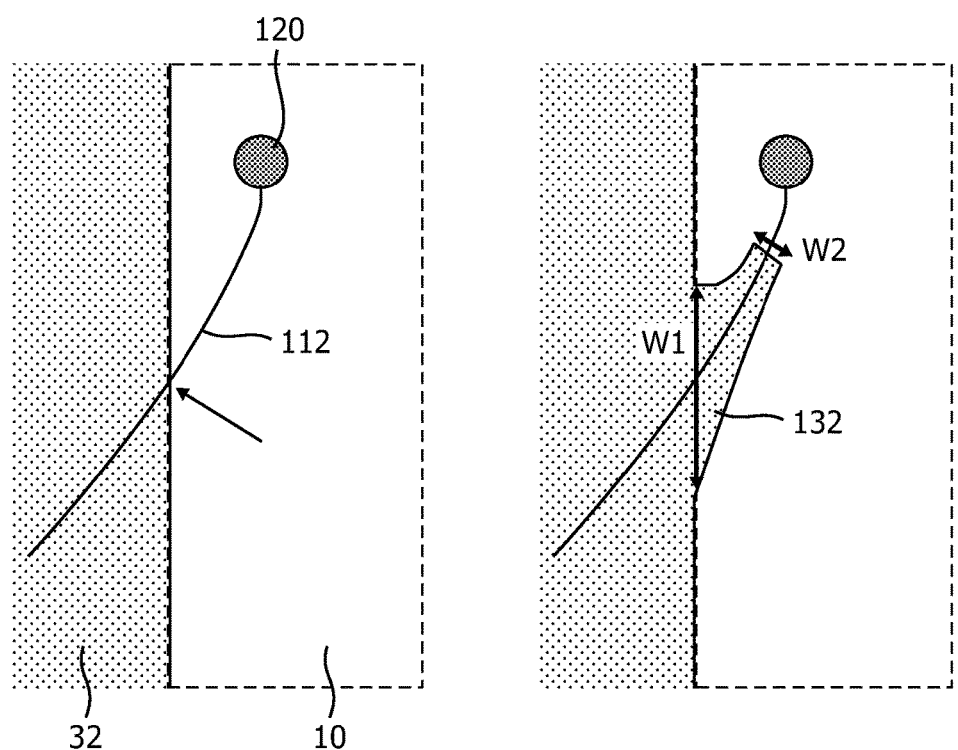
FIG. 14 shows an aspect of a device in accordance with yet another embodiment of the present invention.

Interconnect failure is one of the predominant causes for device failure, especially after a large number of stretch-contraction cycles of the deformable layer 32. As shown in the left pane in FIG. 14, one of the critical points in the device design is the point where interconnect 112 crosses the boundary between the deformable layer 32 and the substrate 10 carrying the bond pad 120. The large difference between the flexibility of the elastomeric deformable layer 32 and the rigid substrate 10 means that the interconnect 112 is subjected to increased stresses at this boundary, where the interconnect 112 already is more prone to failure due to the sharp angle in the interconnect caused by the step from a higher layer, i.e. the deformable layer 32, to a lower layer, i.e. the surface of the substrate 10.

This may be solved by stiffening the deformable layer 32 at its boundary with the substrate 10, e.g. by the inclusion of stiffening structures in the deformable layer 32, but this requires a substantial number of additional processing steps that adds to the complexity and cost of the device. A more cost-effective solution is shown in the right hand pane of FIG. 14, where the deformable layer 32 is shaped to have 'fingers' 132 extending onto the substrate 10, with the interconnects 112 being guided onto the substrate 10 over the fingers 132. The fingers 132 have a tapered shape that taper inwardly away from the deformable layer 32. In other words, the fingers 132 have a width W1 at the deformable layer end that is larger than the width W2 at the substrate end. These tapered extensions restrict the deformation of the layer 32, thereby limiting the variation in the step angle of the interconnect 112 during use of the device 100. The tapered extensions 132 may be formed without the need for additional processing steps, and are therefore a cost-effective way of improving the robustness of the interconnects at these boundaries.

It should be understood that many variations to the device 100 are possible without departing from the present invention.

For instance, it is pointed out that the multi-electrode arrangement of the device 100 of the present invention may be supplemented with a plurality of sensors other than electrodes. Non-limiting examples of such sensors include strain-gauges that can measure the amount of force induced by the contraction of the cardiomyocytes, and micro-calorimeters that can measure the amount of heat produced by these cells.

It is further pointed out that although the embodiments of the device 100 of the present invention have been shown to comprise passive devices only, the interconnect layer including the multi-electrode arrangement may additionally contain active devices for forming circuits that for example can perform the function of signal amplification and signal shaping.

It should be appreciated that the device of the present invention makes it possible to measure the field potential generated by the cardiomyocytes. Field potential prolongation/shortening is directly correlated to action potential prolongation/shortening and can be used to predict the effect of compounds on the QT interval, i.e. the interval representing the duration of ventricular depolarization and subsequent repolarization, measured from the beginning of the QRS complex to the end of the T wave of the heart rhythm; as well as other abnormalities in the electrical activity and rhythm of the cardiomyocyte.

Compared to electrophysiological measurements performed in a steady state system, where cells are cultured on a solid substrate, the device of the present invention resembles native heart tissue. This allows accurate simulation pro-arrhythmic conditions, such as arrhythmias due to long QT syndrome that occur during physical exertion when both heart rate, end-diastolic ventricular volume and filling pressure increase to induce the required increase in cardiac output.

The direct relationship between the level of stretch of the ventricular wall cardiomyocytes and the contraction force of the cardiomyocytes is described in the Frank-Starling law. With increased stretch, contraction force increases until a point is reached where further stretch causes a reduction in cardiac output due to a mismatch between the contractile filaments. The stretch-related increase in contraction force has been described as electromechanical feedback. This (patho-)physiological stretching of the cardiomyocytes 130 plays a role in ion channel activity and proneness to arrhythmias. The stretchable device of the present invention makes it possible to measure ion channel activity through recording of the electrical field potential of the cardiomyocytes under controlled (patho-)physiological conditions of cardiomyocyte stretch and contraction.

With the device such measurements of ion channel activity as described above can also be performed in specific cardiomyocyte-based disease models, such as for example a disease model for hypertrophic cardiomyopathy and for congestive heart failure. A disease model for cardiac hypertrophy can be produced for example by using human stem cell-derived cardiomyocytes which contain the causative gene mutation. A disease model for acute heart failure, for example caused by a myocardial infarction, can probably be produced by pathologic stretching the cardiomyocytes adhered to the stretchable stack of the device of the present invention. Continuous recording of ion channel activity (electrical field potential) and contraction force can be used to monitor disease progression. Such disease model systems can thus be used for drug target discovery, i.e. the identification of specific biological molecules that play a causative role in the disease process, and for the discovery of compounds that can be used to treat the disease, as well as for drug development. Obviously, potential cardiotoxicity of chemical compounds, related to a specific disease state, can also be tested in the relevant disease model systems.

Development of the aforementioned disease models may also require exposure of the live cardiomyocytes 130 to solutions that comprise solutes present in the blood, such as electrolytes, $O_2$, $CO_2$, glucose, certain proteins and metabolites, and so on in concentrations that are known to play a causative role in the simulated disease. Hence, the response of the cardiomyocytes 130 to such solutes can also be used in the search for and validation of drug targets.

A non-limiting example of an experiment to be performed with an embodiment of the device 100 of the present invention may be summarized as follows.

After device production, the grooved deformable layer 32, preferably a PDMS layer, is coated with a bio-adhesive, preferably fibronectin. This is followed by plating a single cell suspension of cardiomyocytes 130 in a suitable culture medium 150 in the reservoir over the grooved deformable layer 32. The device 100 is subsequently placed in an incubator for a sufficient period of time, e.g. 48 hours in the case of a PDMS membrane to complete the adhesion of the cardiomyocytes 130 to the membrane in the self-aligned fashion previously described.

At this stage, immature cardiomyocytes 130 may be stretched for maturation purposes although this step may be omitted. The device 100 may be calibrated by performing a baseline recording in the presence of the medium 150 only.

After calibration, the chemical compound or stimulus of interest is added to the medium 150, and data acquisition is commenced. Depending on the nature of the chemical compound of interest, data acquisition, i.e. compound response measurement, may range from several minutes for an ion channel blocker to several days for other types of chemical compounds of interest. Upon completion of a measurement, the dosage of the compound of interest may be increased and the measurement may be repeated for cumulative dose response curve testing purposes.

It should be obvious to the skilled person that many variations to the above example experiment may be made without departing from the present invention. For instance, after recovery and or maturation of the cardiomyocytes 130, the composition of the culture medium 150 may be varied, e.g. by modifying ion concentration, pH, temperature, hypoxia, and so on. Other variations to the above example experiment will be apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The mere fact that certain measures are recited in mutually different dependent claims does not indicate that a combination of these measures cannot be used to advantage.

The invention claimed is:

1. A device for cardiac electrophysiology screening comprising:
   a substrate comprising a cavity, said substrate carrying a deformable layer configured for out-of-plane deformation extending over said cavity such that a central region of the deformable layer is not attached to the substrate, wherein a portion of said deformable layer covers said cavity, said portion having a surface comprising a pattern of grooves that are formed in the deformable layer and extend only partially through the deformable layer, said portion carrying an electrode structure and a fibronectin adhesive coating;
   a plurality of cardiomyocytes are configured to spontaneously assemble in an aligned and interconnected fashion into the pattern of grooves on the adhesive-coated surface portion of the deformable layer, such that meaningful readings from coordinated stretch/contraction cycles of the cardiomyocytes may be obtained;
   wherein the deformable layer is configured to trigger the assembling of the plurality of cardiomyocytes in the pattern of grooves,
   wherein the pattern of grooves have a dimension lower than 200 microns,
   wherein the electrode structure is formed in the pattern of grooves or on ridges.

2. The device of claim 1, wherein each of said grooves has a pair of side walls, each side wall forming a substantially perpendicular angle with the surface of the deformable layer.

3. The device of claim 1, wherein:
   the portion has a circular shape;
   the grooves extend radially from the center of the portion to at least one region of the deformable layer covering the substrate; and
   the electrode structure comprises at least one spiral electrode.

4. The device of claim 1, wherein the deformable layer comprises opposite ends, wherein said portion is located along an imaginary axis extending between the opposite ends, said portion separating said opposite ends from each other.

5. The device of claim 4, wherein said grooves extend in a direction parallel or perpendicular to said axis.

6. The device of claim 4, wherein the electrode arrangement comprises a plurality of electrodes that over said portion extend in a direction parallel to said axis.

7. The device of claim 1, wherein the deformable layer is a PDMS layer.

8. The device of claim 1, wherein:
an edge of the deformable layer on the substrate comprises a tapered protrusion, said protrusion tapering inwards in a direction away from said portion;
the substrate carries a bond pad; and
the device further comprises an interconnection between the electrode structure and the bond pad, said interconnection extending from the portion to the bond pad over the tapered protrusion.

9. An assembly comprising:
a pressure chamber comprising an inlet;
the device of claim 1, wherein said portion forms a membrane over the pressure chamber; and
a reservoir located over said portion, said pattern of grooves and the electrode structure facing the reservoir.

* * * * *